United States Patent [19]

Xue et al.

[11] Patent Number: 5,792,065

[45] Date of Patent: Aug. 11, 1998

[54] METHOD AND APPARATUS FOR DETERMINING T-WAVE MARKER POINTS DURING QT DISPERSION ANALYSIS

[75] Inventors: Qiuzhen Xue, Germantown; Shankara Reddy, Cedarburg, both of Wis.

[73] Assignee: Marquette Medical Systems, Inc., Milwaukee, Wis.

[21] Appl. No.: 819,075

[22] Filed: Mar. 18, 1997

[51] Int. Cl.⁶ .......................... A61B 5/0452; A61B 5/0402
[52] U.S. Cl. ............................................. 600/516; 600/518
[58] Field of Search .................................... 600/516, 518

[56] References Cited

U.S. PATENT DOCUMENTS

| | | | |
|---|---|---|---|
| 5,348,020 | 9/1994 | Hutson . | |
| 5,419,338 | 5/1995 | Sarma et al. | 128/793 |
| 5,437,285 | 8/1995 | Verrier et al. | 128/702 |
| 5,456,261 | 10/1995 | Luczyk | 128/702 |
| 5,560,368 | 10/1996 | Berger | 128/703 |
| 5,560,370 | 10/1996 | Verrier et al. | 128/705 |

OTHER PUBLICATIONS

Pye M; Quinn AC; Cobbe AM, QT interval dispersion: a non-invasive marker of susceptibility to arrhythmia in patients with sustained ventricular arrhythmias?, British Heart Journal, Jun. 1994, 71: 511–514.

Fei L; Statters DJ; Camm AJ, QT-interval dispersion on 12-lead electrocardiogram in normal subjects: its reproducibility and relation to the T wave, American Heart Journal Jun. 1994, 127: 1654–1655..

Bhullar HK; Fothergill JC; Goddard WP; de Bono DP, Automated measurement of QT interval dispersion from hard-copy ECGs, Journal Electrocardiology, 1993 26:321–331..

Zareba W ; Moss AJ ; le Cessie S, Dispersion of ventricular repolarization and arrhythmic cardiac death in coronary artery disease, American Journal Cardiology, 1994, 74:550–553..

Higham PD, Campbell RWF, QT dispersion –A review, British Heart Journal, 1994, 71:508–510.

Merri M, Benhorin J, Alberti M, Locati E, Moss A, Electrocardiographic quantitation of ventricular repolarization. Circulation 1989, 80:1301–1308.

Moreno FL; Villanueva T; Karagounis LA; Anderson JL, Reduction in QT interval dispersion by successful thrombolytic therapy in acute myocardial infarction. TEAM–2 Study Investigators, Circulation, Jul. 1994, 90:94–100..

Mirvis, J, Spatial variation of QT intervals in normal persons and patients with acute MI, Journal of American College Cardiology, Mar. 1985, 5:625–631.

van de Loo A, Arendts W, Hohnloser SH, Variability of QT Dispersion measurements in the surface ECG in patients with acute myocardial infarction and in normal subjects, American Journal of Cardiology, 1994, 74:1113–1118.

Davey PP; Bateman J; Mulligan IP; Forfar C; Barlow C; Hart G, QT interval dispersion in chronic heart failure and left ventricular hypertrophy: relation to autonomic nervous system and Holter tape abnormalities, British Heart Journal, Mar. 1994, 71:268–273.

(List continued on next page.)

*Primary Examiner*—William E. Kamm
*Assistant Examiner*—Carl H. Layno
*Attorney, Agent, or Firm*—Michael Best & Friedrich LLP

[57] ABSTRACT

A method and apparatus for analyzing QT dispersions in ECG lead signals, comprising acquiring a plurality of ECG lead signals, filtering said signals to remove noise without distorting the T-wave morphology, determining critical T-wave marker points, and calculating QT dispersion and their heart rate corrected values from the determined markers. The apparatus comprises a processor programmed to perform these functions.

42 Claims, 4 Drawing Sheets

OTHER PUBLICATIONS

Sedgwick ML; Rasmussen HS; Cobbe SM. Effects of the class III antiarrhythmic drug dofetilide on ventricular monophasic action potential duration and QT interval dispersion in stable angina pectoris. American Journal Cardiology, Dec. 1992, 70:1432–1437.

Day CP, McComb JM, Campbell RWF. Reduction in QTD by sotalol following myocardial infarction. European Heart Journal, 1991, 12:423–427.

Cui G, Sager P, Uppal P, and Singh BN. Effects of Amiodarone, Sematilide, and Sotalol on QT dispersion. American Journal Cardiology, 1994, 74:896–900.

Priori SG; Napolitano C; Diehl L; Schwartz PJ. Dispersion of the QT interval. A marker of therapeutic efficacy in the idiopathic long QT syndrome. Circulation, 1994, 89:1681–1689.

Zareba W; Badilini F; Moss AJ. Automatic detection of spatial and dynamic heterogeneity of repolarization. Journal of Electrocardiology, 1994, 27 Suppl pp. 66–72.

Day CP, McComb JM, Campbell RWF. QT dispersion: An indication of arrhythmia risk in patients with Long QT intervals. British Heart Journal, 1990, 63:342–344.

DeAmbroggi L, et al. Dispersion of ventricular repolarization in the Long QT Syndrome. American Journal of Cardiology, 1991, 68:614–620.

METHOD AND APPARATUS FOR DETERMINING T-WAVE MARKER POINTS DURING QT DISPERSION ANALYSIS

BACKGROUND OF THE INVENTION

The QT interval of a surface electrocardiogram is the time between the QRS onset and the end of the T-wave. QT dispersion is a measure of differences in the QT interval as measured in different ECG leads. One measure of QT dispersion is the difference between the longest and the shortest QT intervals; the other measure is the standard deviation of QT intervals measured from all the ECG leads. Recent research has found that increased QT dispersion is an indicator of malignant arrhythmias. Clinically, the QT dispersion may be used to monitor the effects of antiarrhythmic drugs and ventricular repolarization times. In most cases, QT dispersions were measured manually, where, the end of the T-wave was determined by measuring the point where the T-wave returns to the isoelectric line. However, interobserver and intraobserver differences in the QT dispersion were found in several studies. It is even more difficult to obtain consistent measurements in ECGs with noise or irregular T-wave shapes. For this reason, computerized automatic methods of measuring T-end and T-peak have been developed.

Markers for obtaining an objective and consistent measurement of T-wave end as proposed in these studies are: (a) the point where the T-wave crosses the isoelectric line plus a threshold; (b) the intersection of the final slope of the T-wave and a threshold level which is a fraction of the amplitude of the last peak of the T-wave; (c) the intersection of the final slope of the differential of the T-wave and a threshold level which is a fraction of the amplitude of the last peak of the differential of the T-wave; (d) the point where the T-wave area reached a certain percentage (90%) of the whole T-wave area. Method (a) has the same problem as the manual method and methods (b) and (c) have difficulty in finding a stable maximum slope point in determining the thresholds. Method (d) has not proven to be useful in differentiating low risk patients from high risk patients.

There is a need to provide a T-wave marker in which the QT dispersion measurement has a good reproducibility and a good differentiation between low and high risk groups. It is well known that T-waves are not as clearly defined morphologically as QRS in both time and frequency domains. Therefore, any measurement method relying on a single point is susceptible to noise and to changes in T-wave shape.

SUMMARY OF THE INVENTION

It is an object of the invention to provide a new and improved method and apparatus for determining QT dispersion in ECG wave forms.

A further object of the invention is to provide a method and apparatus for determining the peak and end of the T-wave portion of an ECG wave form.

Another object of the invention is to provide a method and apparatus for determining T-wave markers in which the QT dispersion measurement has a high degree of reproducibility.

A still further object of the invention is to provide a method and apparatus for providing T-wave markers in which the QT dispersion measurement has a high degree of differentiation between low and high risk groups.

Yet another object of the invention is to provide a method and apparatus for making QT dispersion measurements which do not rely on a single reference point.

It is a further object of the invention to provide a method and apparatus for making QT dispersion measurements whose accuracy are not susceptible to noise or changes in T-wave shapes.

These and other objects and advantages of the invention will become more apparent from the detailed description thereof taken with the accompanying drawings.

In general terms, the method comprises a method of analyzing QT dispersions in ECG lead signals, comprising the steps of: acquiring a plurality of ECG lead signals, filtering said signals to remove noise without distorting the T-wave morphology, determining critical T-wave marker points, and calculating QT dispersion and their heart rate corrected values from the determined markers.

According to a more specific aspect of the invention, the filtering step comprises storing each of said ECG lead signals in a column-wise matrix and reconstructing each ECG signal by decomposing the matrix by the dimension reduction technique.

According to a further aspect, the invention includes the step of generating a detection function from the absolute difference between successive samples of at least some of the reconstructed ECG signals and determining the T-peak from the valley points of the detection functions. According to one embodiment, the valley point of the detection function are determined by regional centering.

Yet another more specific aspect of the invention is the step of determining critical T-wave marker points includes the steps of determining T-end from the intersection of a least-square fitted line around the maximum slope of the reconstituted ECG signals after T-peak and a threshold value plus a non-linear correction function based on T-wave amplitude. According to another embodiment, the step of determining critical T-wave marker points includes the steps of generating templates of at least some of the ECG lead signals and matching measured ECG signals to said templates.

The invention also comprises an apparatus for analyzing QT dispersions in ECG lead signals and including: means for acquiring a plurality of ECG lead signals, means for filtering said signals to remove noise without distorting the T-wave morphology, means for determining critical T-wave marker points, and means for calculating QT dispersion and their heart rate corrected values from the determined markers.

According to a more specific aspect of the invention, the filtering comprises means for storing each of said ECG lead signals in a column-wise matrix and means for reconstructing each ECG signal by decomposing the matrix by the dimension reduction technique.

According to another aspect, the invention includes means for generating a detection function from the absolute difference between successive samples of at least some of the reconstructed ECG signals and means for determining the T-peak from the valley points of the detection functions.

The invention also contemplates means for determining the T-peak includes means for the regional centering of the valley points.

According to a further aspect of the invention, the means for determining critical T-wave marker points includes the means for determining T-end from the intersection of the maximum slope of the reconstituted ECG signals after T-peak and the threshold plus a non-linear correction function based on T-amplitude.

In another embodiment, the means for determining critical T-wave marker points includes the steps of generating templates of at least some of the ECG lead signals and matching measured ECG signals to said templates.

DETAILED DESCRIPTION OF THE PREFERRED EMBODIMENT

Figure 1:
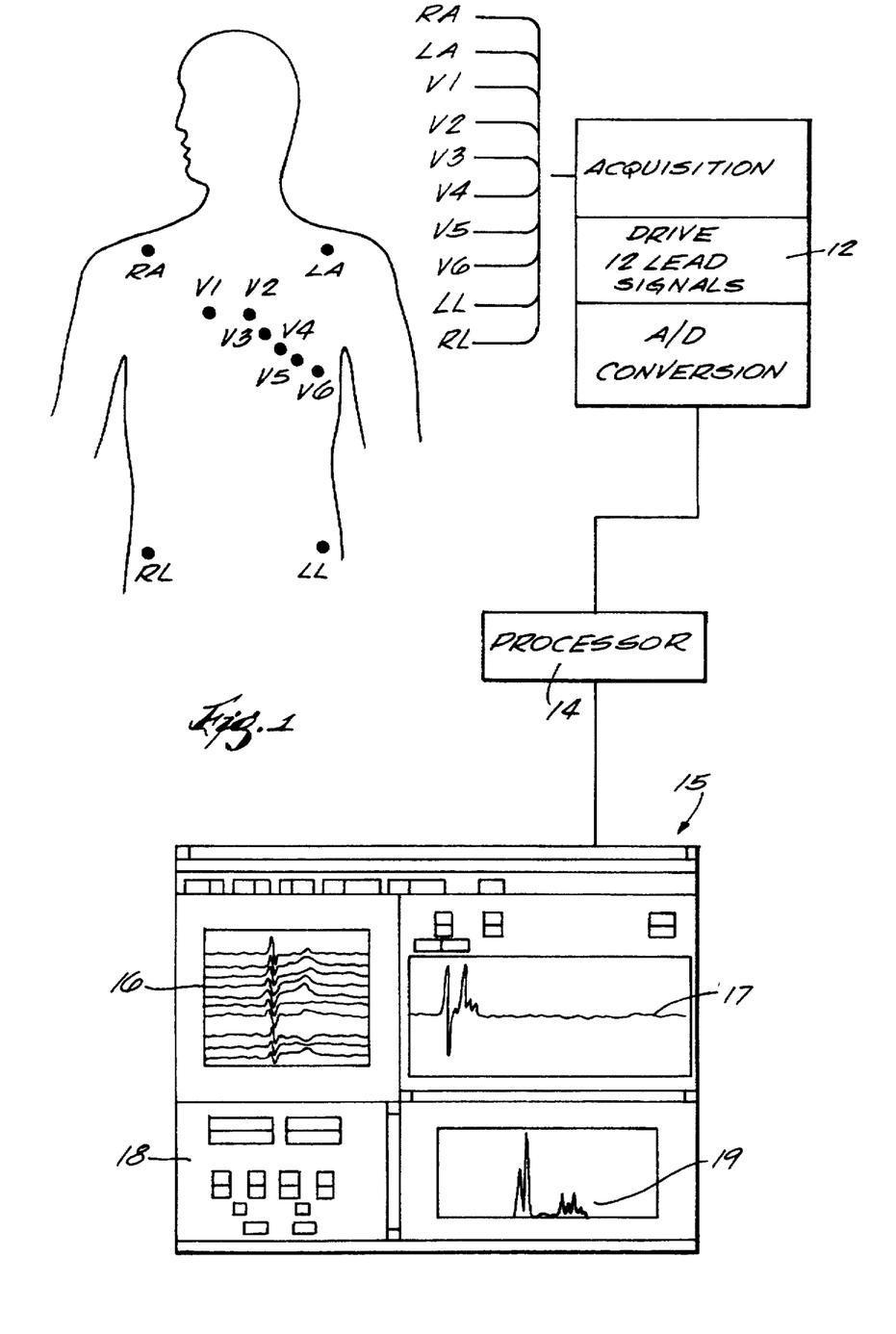
FIG. 1 schematically illustrates a cardiac monitor and twelve lead analyzing system according to the invention.

FIG. 1 schematically illustrates the cardiac monitor and twelve lead analyzing system according to the present invention. The system includes a conventional data acquisition module 12 which is connected by lead wires to ten or fourteen electrodes positioned on the patients body. In the illustrated embodiment, the electrodes are located to provide twelve leads of ECG signals. In particular, the electrodes include a right arm electrode RA; a left arm electrode LA; chest electrodes V1, V2, V3, V4, V5 and V6; a right leg electrode RL and a left electrode leg LL. For the acquisition module connected to fourteen electrodes, the additional chest electrodes positions are V3R, V4R, and V8, or any combination of the right ventricular and posterior chest locations. The acquisition module 12 includes conventional common mode rejection and filters for removing patient breathing and muscle artifacts. The acquisition module converts the analog lead signals to digital signals and generates conventional ECG leads I, II, V1, V2, V3, V4, V5, V6, V3R, V4R, and V8 which are acquired directly for the patient leads and leads III, aVR, aVF and aVL, which are derived using Einthoven's law. The combination of electrode signals used for determining or deriving the ECG lead signals are well known in the art and will not be discussed here for the sake of brevity. The digitized ECG signals are provided to a processor 14 for twelve or fifteen leads and a QT dispersion and repolarization analyses.

Figure 2:
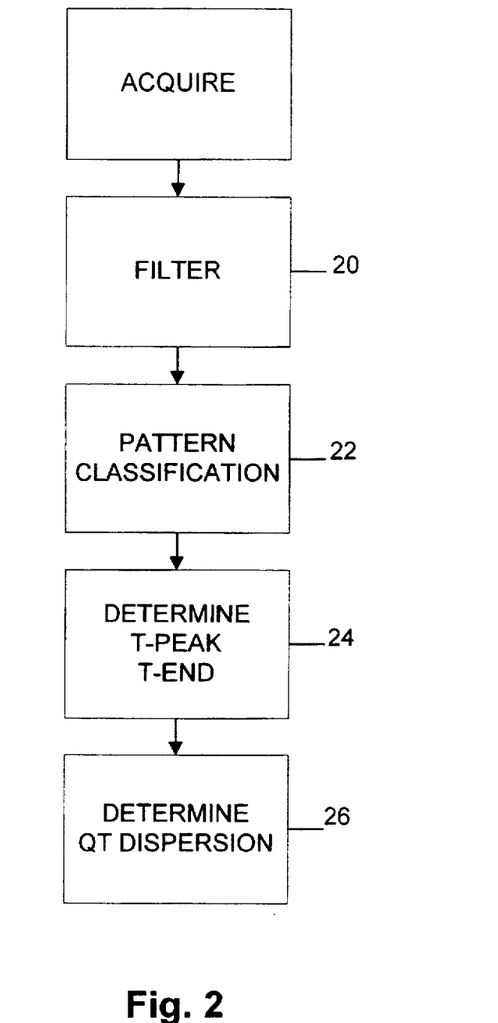
FIG. 2 is a block diagram showing the method of determining QT dispersion according to the preferred embodiment of the invention.

The processor 14 is programmed to perform the method illuistrated in FIG. 2 and forms a part of a QT dispersion analyzer 15. The analyzer is a personal computer running either on Microsoft Windows 95 or Microsoft Windows NT operating system. The main purpose of the analyzer is to analyze a large number of ECGs so that these ECGs can be reviewed on the first window 16 of the analyzer 15. The system also automatically detects T-offset and T-peak and computes QT dispersion, QT peak dispersion, and their heart rate corrected value which are displayed in the second window 18. In addition, the QT parameters are automatically detected for a group of ECG files in a batch mode and these results are saved in the Microsoft Access database. In addition, the QT map of the twelve lead ECG may also be displayed in window 19. In addition, there is a review function which allows the user to review the processed ECG data in window 17 and to modify the T-offset in T-peak if necessary. Finally, user may copy these ECG files from a floppy diskette to hard disk without overlapping file names and to print a report of the QT dispersion results.

Figure 3:
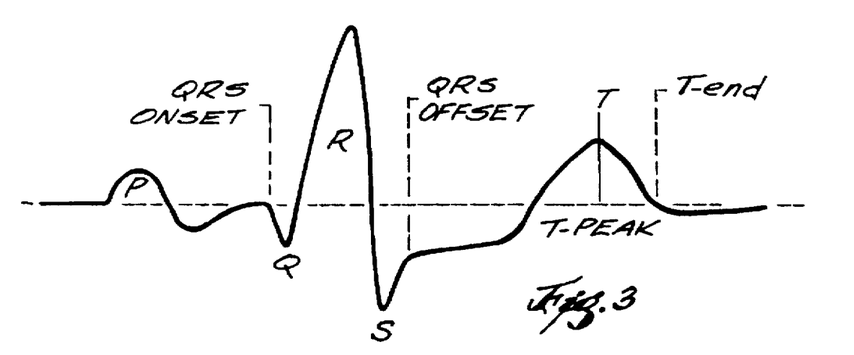
FIG. 3 shows ECG markers.

The processor 14 is programmed to perform the method or functions illustrated in FIG. 2, which is a block diagram showing the method of determining QT dispersion according to the preferred embodiment of the invention. The method or program includes the steps of filtering the ECG lead signals to reduce noise without distorting the T-wave morphology. The filtered signals are then classified into different groups such as upright, inverted, biphasic or TU combination. Critical markers such as T-wave peak and T-wave end are determined. The QT dispersions are then calculated and their heart-rate values corrected based on determined markers. The markers are determined by measuring the fiducial points across all twelve leads, such as QRS onset and QRS offset. It has been shown that the dispersion of QRS onset across twelve leads is much smaller than the dispersion of the T-wave end. Therefore, the same QRS onset for all 12 leads may be used. The global offset point may be calculated as an initial reference for searching T-wave markers of individual leads. These markers are illustrated in FIG. 3. The programmed computer includes means for performing the functions illustrated in the block diagram of FIG. 2 and specifically means 20 for filtering the ECG signals to remove noise without distorting the T-wave morphology, means 22 for classifying the T-waves into different groups, means 24 for determining critical T-wave marker points and means 26 for calculating QT dispersion.

The filtering step is based on a dimension reduction technique of Singular-Value-Decomposition (SVD). This technique is discussed in *Numerical Recipes in C, The Art of Scientific Computing*, by William H. Press, Saul A. Teukolsky, Brian P. Flannery and William T. Vetterling, Cambridge University Press (1988), pp. 60–71 and 534–539 which is incorporated by reference herein. SVD is based on the theorem of linear algebra that any $U \times S$ matrix A whose number of rows U is greater or equal to the number of columns S, can be written as the product of an $U \times S$ column-orthogonal matrix $U_1$, an $U \times S$ diagonal matrix $S_1$, with positive or zero elements and the transpose of an $U \times S$ orthogonal matrix V. The shapes of these matrices are illustrated below $$(A) = (U) \cdot \begin{pmatrix} S_1 & & & & \\ & S_2 & & & \\ & & \cdot & \cdot & \\ & & \cdot & \cdot & \\ & & \cdot & \cdot & \\ & & & & S_n \end{pmatrix} \cdot (V^T)$$

The matrices U and V are orthogonal in the sense that their columns and orthonormal $$\sum_{i=1}^{M} U_{ik} U_{in} = \delta_{kn} \quad \begin{array}{l} 1 \leq k \leq N \\ 1 \leq n \leq N \end{array}$$

$$\sum_{j=1}^{N} U_{jk} U_{jn} = \delta_{kn} \quad \begin{array}{l} 1 \leq k \leq N \\ 1 \leq n \leq N \end{array}$$

or as a table $$(U^T) \cdot (U) = (V^T) \cdot (V) = (1)$$

Since V is square, it is also row-orthonormal. $V \cdot V^T = 1$.

The twelve or fifteen lead ECG signals are stored and in a column-wise matrix in which the first row comprises the digital signals representing the first sample in each lead and the first column comprises the samples in the first lead and so on. SVD dimension reduction technique decomposes the A matrix into three matrices:

$$A = USV^T$$

where: U and V are each orthogonal matrices in the sense that their columns are orthonormal;

S is a diagonal matrix called a singular matrix which also can be denoted $|s_1, s_2, \ldots s_n|$ diag' whose elements have monotonically decreasing values, i.e. $s_1 > s_2 > \ldots > s_n$.

After analyzing more than one hundred ECGs, it has been found that the first three diagonal components contribute more than 98% of the total energy i.e.

$$\frac{S_1^2 + S_2^2 + S_3^2}{\sum_{i=1}^{N} S_i^2} > .98$$

Figure 4:
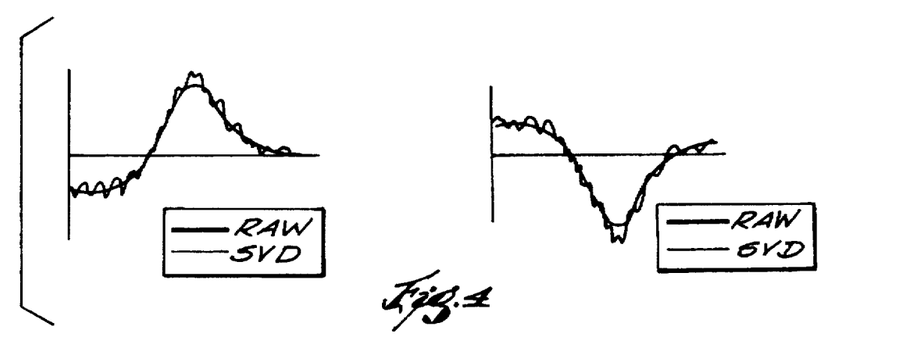
FIG. 4 shows T-waves which were reconstructed in accordance with the method of the invention.

Therefore, the ECGs can be reconstructed using the first three components of each matrix. In this way, $U_1$ can be taken as a subset of the U matrix whose first three columns are used, and $V_1$ as a subset V whose first three rows are used, and $S_1$ as a subset of S whose first three elements are used. The new twelve or fifteen lead ECGs are reconstructed as: $A_1 = U_1 S_1 V_1^T$ Two reconstructed T-waves along with their originals are displayed in FIG. 4. It can be seen that reconstructed T-waves are smoother than the originals but without any phase distortion and prolongation which usually occurs when conventional digital filters are used. It was also found that by using the first four components, the QRS portion of the twelve-lead ECG signal can be reconstructed with high accuracy.

Figure 5:
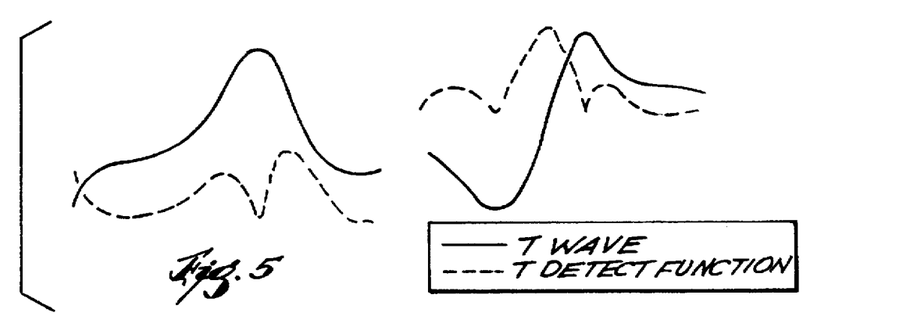
FIG. 5 illustrates reconstructed T-waves and their detection functions derived in accordance with the invention.

T-wave morphology can be categorized into several main patterns using a T-wave detection function. These patterns include monophasic with upright T (most normal ECGs), monophasic with inverted T, biphasic T and T-U combination. To form the detection function, the difference between successive samples of the SVD reconstructed T-wave and the absolute value is used. Two examples of T-wave detection function are shown in FIG. 5. It can be seen that: (1) all values are positive in the T detection function; (2) the peaks in the detection function correspond to maximum slopes (up-slope or down-slope) of the original T-wave; and (3) the valleys in the detection function correspond to the peaks in the original T-waves. This T-wave detection function removes possible baseline drift and enhances the features of the T-waves. Because the T-wave peak may be irregular or lie in a relatively flat plateau, the T-wave peak can more easily be identified from the valley in the detection function.

For pattern recognition, the patterns based on the morphology of the detection function can be summarized as follows:

(1) Both the morphasic upright and inverted T-waves have the same features in the detection function that is, two peaks and one valley; (2) the biphasic T-waves have more than three peaks and two valleys; and (3) the U-wave adds more peaks and valleys to the major peaks in the detection function.

As can be seen, the T-wave peak may be determined from the valley points of the detection function. However, the situation is more complex since the T-wave peaks are not clearly defined as are the peaks of the QRS wave form. In most cases, there is a plateau around the T-wave peak, especially for low amplitude T-waves. Accordingly, a regional centering step is employed to overcome this problem. The region around the valley point of the detection function is:

where:

$$\{Pt_x | T_p - Th < Y_x < T_p + Th\}$$

$Pt_x$ are the sample points of the T-wave.

$T_p$ is the peak point defined by the detection function.

Th is the regional threshold and $Y_x$ is the amplitude of the T-wave around $T_p$.

The center point of this region is defined as the final T-peak. This method has been found to be more reproducible than directly using the valley point of the detection function as the T-peak.

Figure 6:
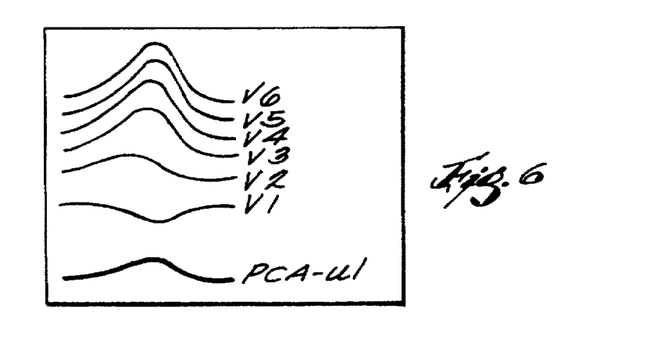
FIG. 6 shows six precordial leads of ECG and their first principal vector as a template for pattern matching.

Another method for finding the T-peak is a template matching based on the SVD technique. For those T-waves that have been recognized as monophasic, an SVD analysis was performed. The T-wave template is the first column of the U matrix as shown in FIG. 6, which is the vector of the first principal component. This template may be used to match the T-wave in a sliding window of the display 15 of FIG. 1. The T-peak is defined as the point where the template and the T-wave have the largest correlation coefficient. This method is more accurate than the regional-centering method, since it uses a whole template instead of relying on just a few points.

Figure 7:
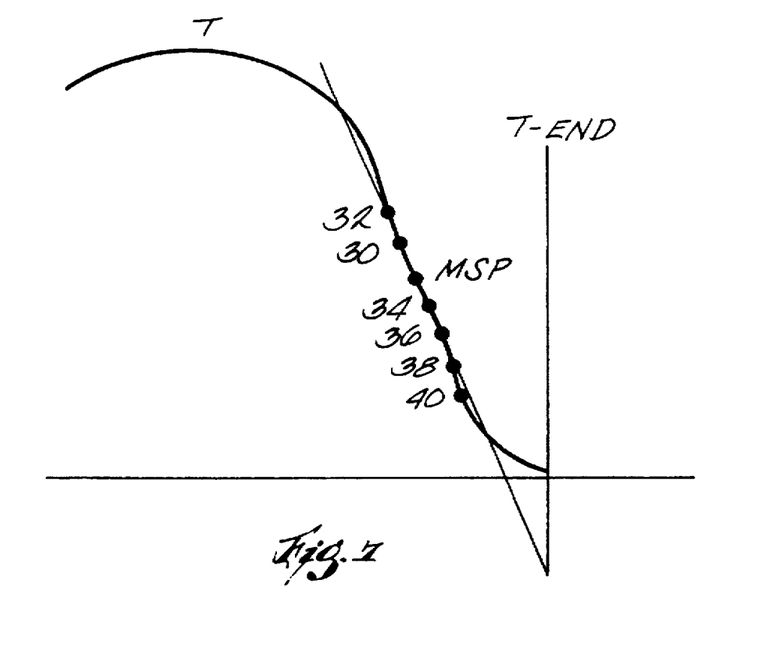
FIG. 7 illustrates the least squares method of determining the T-wave end.
Figure 8:
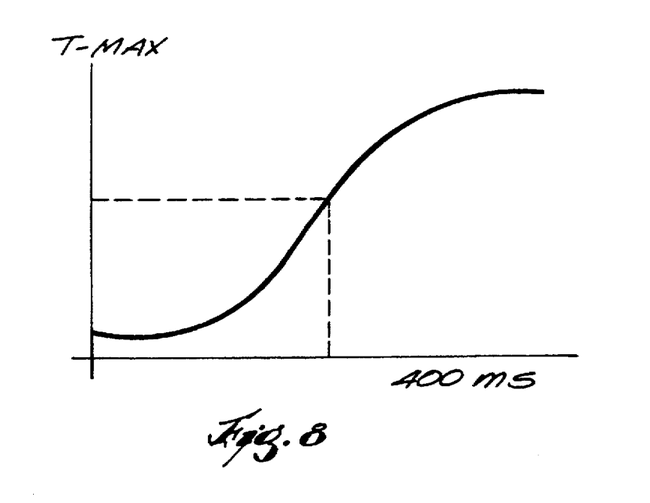
FIG. 8 shows the correction factor for determining T-wave end.

After locating the T-peak, the maximum slope point (MSP) after the final T-peak is used to find the T-end. Instead of using the tangent of MSP, which could be more subject to noise, several neighbor points around the MSP may be analyzed. As shown in FIG. 7, the region includes two points 30, 32 prior to the MSP, the MSP itself, and four points 34, 36, 38, 40 after the MSP. The least-square method may be used to fit a straight line to this region as shown in FIG. 7. Another line is drawn with a threshold defined in the T-P segment, which is the baseline plus one standard deviation in the window. The intersection of these two lines is defined as an initial T-end. A non-linear correction based on the amplitude of the T-peak is then applied to the initial T-end. This correction as shown in FIG. 8 in which the correction in milliseconds plotted against T-peak. For the T-U case, the T-end is further extended to the nadir between the T-wave and U-waves.

Based on the T-peak and T-end points, QT dispersions may be calculated. First, those leads with any of the following conditions are eliminated:

(a) Very noisy;

(b) Very flat T-wave;

(c) T-waves with undefined patterns.

For the T-peak dispersion, those leads with biphasic T-waves are eliminated.

Since the QT interval in milliseconds varies with the heart beats per minute (bpm), the T peak dispersion will also vary with the number of bpm. The dispersion for all 12-leads (global) and six prechordal leads (prechordal) are corrected according to heart rate using the well known Bazett's formula as follows:

$$QT_C = QT \cdot \sqrt{HR/60}$$

where $QT_c$ = Corrected QT interval

QT = calculated QT interval

HR = heart rate in bpm.

For the dispersion, the difference between the maximum and minimum QT intervals are used i.e. the difference between the maximum QT-end (or QT-peak) and the minimum QT-end or QT-peak. Another measure of QT of dispersion can be based on the standard deviation of all QT values.

It has been found that the results obtained in determining QT dispersion in accordance with the invention is more reproducible that is, having lower mean differences in dispersion than with other known methods.

I claim:

1. A method of analyzing QT dispersions in ECG lead signals, comprising the steps of:

acquiring a plurality of ECG lead signals, filtering said signals to reduce noise without distorting the T-wave morphology, determining critical T-wave marker points, calculating QT dispersion and their heart rate corrected values from the determined T-wave maker points.

2. The method set form in claim 1 and including the step of classifying the T-waves into different groups.

3. The method set forth in claim 1 wherein said filtering step comprises storing each of said ECG lead signals in a column-wise matrix and reconstructing each ECG signal by decomposing the matrix by the dimension reduction technique.

4. The method set forth in claim 1 wherein the step of determining critical T-wave maker points comprises the steps of determining T-wave peak and T-wave end.

5. The method set forth in claim 1 wherein said filtering step comprises storing each of said ECG lead signals in a column-wise matrix A and reconstructing each ECG signal by decomposing the matrix A by the dimension reduction technique into three matrices:

$$A_1 = U_1 S_1 V_1^T$$

where: U and V are each orthogonal matrices:

S is a diagonal matrix: $|S_1, S_2, \ldots S_k|$diag whose elements have monotonically decreasing values, i.e., $S_1 > S_2 > \ldots > S_k$; and k<n, original dimension.

6. The method set forth in claim 5 and including the step of generating a detection function from the absolute difference between successive samples of at least some of the reconstructed ECG signals and determining the T-peak from the valley points of the detection functions.

7. The method set forth in claim 6 and including the step of determining the valley point of the detection function by regional centering.

8. The method set forth in claim 7 wherein the step of determining critical T-wave marker points includes the steps of determining T-end from the intersection of the maximum slope of the reconstituted ECG signals after T-peak and a threshold value plus a non-linear correction function based on T-wave amplitude.

9. The method set forth in claim 8 and including the steps of disregarding those ECG signals which are noisy, have flat T-waves or T-waves with undefined patterns.

10. The method set forth in claim 9 and including the step of classifying the T-waves into different groups.

11. The method set forth in claim 6 wherein the step of determining critical T-wave marker points includes the steps of generating templates of at least some of the ECG lead signals and matching measured ECG signals to said templates.

12. The method set forth in claim 11 and including the steps of disregarding those ECG signals which are noisy, have flat T-waves or T-waves with undefined patterns.

13. The method set forth in claim 12 and including the step of classifying the T-waves into different groups.

14. The method set forth in claim 1 and including the steps of determining the absolute difference between successive samples of at least some of the reconstructed ECG signals, generating a detection function from said absolute difference, and determining the T-peak from the valley points of the detection functions.

15. The method set forth in claim 14 wherein the steps of determining the valley point of the detection function comprises regional centering.

16. The method set forth in claim 14 wherein the step of determining critical T-wave marker points includes the steps of determining T-end from the intersection of the least-square fitted line around the maximum slope of the reconstituted ECG signals after T-peak and the threshold plus a non-linear correction function based on T-amplitude.

17. The method set forth in claim 16 and including the steps of disregarding those ECG signals which are noisy, have flat T-waves or T-waves with undefined patterns.

18. The method set forth in claim 14 wherein the step of determining critical T-wave marker points includes the steps of generating templates of at least some of the ECG lead signals and matching measured ECG signals to said templates.

19. The method set forth in claim 18 and including the step of disregarding those ECG signals which are noisy, have flat T-waves or T-waves with undefined patterns.

20. Apparatus for analyzing QT dispersions in ECG lead signals, said apparatus including:

means for acquiring a plurality of ECG lead signals, means for filtering said signals to reduce noise without distorting the T-wave morphology, means for determining critical T-wave marker points, and means for calculating QT dispersion and their heart rate corrected values from the determined markers.

21. The apparatus set forth in claim 20 and including means for classifying the T-waves into different groups.

22. The apparatus set forth in claim 20 wherein means for filtering comprises means for storing each of said ECG lead signals in a column-wise matrix and means for reconstructing each ECG signal by decomposing the matrix by the dimension reduction technique.

23. The apparatus set forth in claim 20 wherein said means for filtering comprises means for storing each of said ECG lead signals in a column-wise matrix A and means for reconstructing each ECG signal by decomposing the matrix A by the dimension reduction technique into three sub-matrices:

$$A_1 = U_1 S_1 V_1^T$$

where: U and V are each orthogonal matrices:

S is a diagonal matrix: $[S_1, S_2, \ldots S_k]$diag whose elements have monotonically decreasing values, i.e., $S_1 > S_2 > \ldots > S_k$.

24. The apparatus set forth in claim 20 wherein the means for determining critical T-wave marker points comprises means for determining T-wave peak and T-wave end.

25. The apparatus set forth in claim 20 and including means for generating a detection function from the absolute difference between successive samples of at least some of the reconstructed ECG signals and means for determining the T-peak from the valley points of the detection functions.

26. The apparatus set forth in claim 25 wherein the means for determining the T-peak includes means for the regional centering of the valley points.

27. The apparatus set forth in claim 25 wherein the means for determining critical T-wave marker points includes means for determining T-end from the intersection of the maximum slope of the reconstituted ECG signals after T-peak and the threshold plus a non-linear correction function based on T-amplitude.

28. The apparatus set forth in claim 25 and including means for disregarding those ECG signals which are noisy, have flat T-waves or T-waves with undefined patterns.

29. The apparatus set forth in claim 25 wherein the means for determining critical T-wave marker points includes means for generating templates of at least some of the ECG lead signals and matching measured ECG signals to said templates.

30. The apparatus set forth in claim 29 and including means for disregarding those ECG signals which are noisy, have flat T-waves or T-waves with undefined patterns.

31. The apparatus set forth in claim 20 and including means for generating a detection function from the absolute difference between successive samples of at least some of the reconstructed ECG signals and means for determining the T-peak from the valley points of the detection functions.

32. The apparatus set forth in claim 31 wherein the means for determining the T-peak includes means for the regional centering of the valley points.

33. The apparatus set forth in claim 32 wherein the means for determining critical T-wave marker points includes means for determining T-end from the intersection of the maximum slope of the reconstituted ECG signals after T-peak and the threshold plus a non-linear correction function based on T-amplitude.

34. The apparatus set forth in claim 33 and including means for disregarding those ECG signals which are noisy, have flat T-waves or T-waves with undefined patterns.

35. The method set forth in claim 34 and including means for classifying the T-waves into different groups.

36. The apparatus set forth in claim 32 wherein the means for determining critical T-wave marker points includes means for generating templates of at least some of the ECG lead signals and matching measured ECG signals to said templates.

37. The apparatus set forth in claim 36 and including means for disregarding those ECG signals which are noisy, have flat T-waves or T-waves with undefined patterns.

38. The apparatus set forth in claim 37 and including means for classifying the T-waves into different groups.

39. A method of analyzing QT dispersions in acquired ECG lead signals, comprising the steps of:

determining critical T-wave markers of the acquired ECG signals, calculating QT dispersion and their heart rate corrected values from the determined T-wave markers.

40. The method set forth in claim 39 wherein the step of determining the T-wave markers comprises determining T-peak and T-end.

41. Apparatus for analyzing QT dispersions acquired in ECG lead signals, said apparatus including:

means for determining critical T-wave markers, and means for calculating QT dispersion and their heart rate corrected values from the determined T-wave markers.

42. The method set forth in claim 41 and wherein the means for determining the T-wave markers comprises means for determining T-wave peak and T-wave end.

* * * * *